US012559715B2

(12) United States Patent
Li et al.

(10) Patent No.: US 12,559,715 B2
(45) Date of Patent: Feb. 24, 2026

(54) CELL GROWTH PROMOTER AND APPLICATION THEREOF

(71) Applicant: China Agricultural University, Beijing (CN)

(72) Inventors: Yixuan Li, Beijing (CN); Weibo Zhang, Beijing (CN); Yinhua Zhu, Beijing (CN); Pengjie Wang, Beijing (CN); Yanan Sun, Beijing (CN); Juan Chen, Beijing (CN); Liang Zhao, Beijing (CN); Ruixin Zhu, Beijing (CN); Ran Wang, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 18/668,297

(22) Filed: May 20, 2024

(65) Prior Publication Data

US 2025/0019646 A1     Jan. 16, 2025

(30) Foreign Application Priority Data

Jul. 12, 2023     (CN) ......................... 202310847627.X

(51) Int. Cl.
*C12N 5/00*          (2006.01)
(52) U.S. Cl.
CPC ........ *C12N 5/0037* (2013.01); *C12N 2500/24* (2013.01); *C12N 2500/90* (2013.01); *C12N 2501/998* (2013.01)
(58) Field of Classification Search
None
See application file for complete search history.

(56) References Cited

U.S. PATENT DOCUMENTS

| | | | | |
|---|---|---|---|---|
| 5,573,937 | A * | 11/1996 | Shinmoto .............. | C12N 5/005 435/404 |
| 7,700,352 | B2 * | 4/2010 | Niwa ................... | C12N 5/0606 435/375 |
| 2002/0076747 | A1 | 6/2002 | Price et al. | |
| 2012/0264208 | A1 | 10/2012 | Chen | |

FOREIGN PATENT DOCUMENTS

| | | | | |
|---|---|---|---|---|
| CN | 1349386 A | * | 5/2002 | ........... A23C 9/1522 |
| CN | 113234657 A | | 8/2021 | |
| EP | 0166130 A2 | | 1/1986 | |
| KR | 20180002248 A | * | 1/2018 | ........... A61K 9/5192 |
| WO | WO-2018043450 A1 | * | 3/2018 | ............. A23L 33/10 |
| WO | 2018203834 A1 | | 11/2018 | |
| WO | 2021006733 A1 | | 1/2021 | |

OTHER PUBLICATIONS

Ruan et al., "The Effect of Different Chicken Ovalbumin Extracts on Cell Proliferation", Indian Journal of Animal Research, published online May 9, 2022, DOI: 10.18805/IJAR.BF-1497, pp. 1-4. (Year: 2022).*
Kaipparettu et al., "Novel Egg White-based 3-D Cell Culture System", BioTechniques, 2008, vol. 45, pp. 165-171. (Year: 2008).*
Machine translation for CN 1349386 A, Scherer et al. "Iron Strengthening System" (Year: 2002).*
Zhang et al., "The modification of ovalbumin surface properties treated by pulsed electric field combined with divalent metal ions", Food Chemistry, 2019, vol. 293, pp. 455-462. (Year: 2019).*
Kukutsch et al, "Formation and Kinetics of MHC Class I-Ovalbumin Peptide Complexes on Immature and Mature Murine Dendritic Cells", Journal of Investigative Dermatology, 2000, vol. 115, Issue 3, pp. 449-453. (Year: 2000).*
Nisbet et al., "The Complete Amino-Acid Sequence of Hen Ovalbumin", European Journal of Biochemistry, 1981, vol. 115, pp. 335-345. (Year: 1981).*
Fussl et al., "Cracking Proteoform Complexity of Ovalbumin with Anion Exchange Chromatography-High-Resolution Mass Spectrometry under Native Conditions", Journal of Proteome Research, 2019, vol. 18, pp. 3689-3702. (Year: 2019).*
Sik et al., KR 2018-0002248, machine translation, 2018 (Year: 2018).*
Hideo et al., WO 2018-043450, machine translation, 2018. (Year: 2018).*
Zemser et al., "Relationship Between Functional Properties and Structure of Ovalbumin", Journal of Protein Chemistry, 1994, vol. 13, No. 2, pp. 261-274. (Year: 1994).*
Mine et al., "Fine mapping and structural analysis of immunodominant IgE allergenic epitopes in chicken egg ovalbumin", Protein Engineering, 2003, vol. 16 No. 10 pp. 747-752. (Year: 2003).*
Huntington et al., "Structure and properties of ovalbumin", Journal of Chromatography B: Biomedical Sciences and Applications, 2001, vol. 756, Issues 1-2, pp. 189-198. (Year: 2001).*
Kanaka et al., "A review on ovalbumin gene in poultry", Journal of Entomology and Zoology Studies, 2018; 6(4): 1497-1503. (Year: 2018).*
Bi-Zhen Zhong, et al., Effect of Microwave Irradiation Nonuniformity on the Digestion and Allergenicity of the Glycated Ovalbumin, Journal of Food and Nutrition Research, 2020, pp. 216-224, vol. 8 No. 5.

* cited by examiner

*Primary Examiner* — Laura Schuberg

(57)          ABSTRACT

A cell growth promoter and an application thereof are provided. The invention adopts $Fe^{2+}$ and ovalbumin to form a $Fe^{2+}$-ovalbumin (OVA) compound to promote ovalbumin cell endocytosis, the cell growth promoter can maintain cell growth in an environment free of amino acids, promote cell proliferation in an environment with amino acids; and, the $Fe^{2+}$-OVA compound can replace expensive animal serum albumin in cell culture, the cell growth promoter has a significant effect on improving cell viability and is low cost.

3 Claims, 7 Drawing Sheets

CELL GROWTH PROMOTER AND APPLICATION THEREOF

CROSS REFERENCE TO THE RELATED APPLICATIONS

This application is based upon and claims priority to Chinese Patent Application No. 202310847627.X, filed on Jul. 12, 2023, the entire contents of which are incorporated herein by reference.

TECHNICAL FIELD

The present disclosure belongs to the technical field of biotechnology, and specifically to a cell growth promoter and application thereof.

BACKGROUND

Protein is an essential nutrient for the growth of a body. Researchers often promote cell proliferation or maintain cell activity by adding fetal bovine serum. The fetal bovine serum is rich in protein such as serum albumin, globulin, fibronectin, and transferrin, and the proportion of bovine serum albumin accounts for more than 50% of total protein. The serum albumin is also an important nutrient in the body. The body consumes 14 g/70 kg of serum albumin per day, while the liver synthesizes an equal amount of serum albumin to maintain balance. In the body of a healthy person, fats and proteins provide energy in a ratio of 15:1; and in a patient having cancer, the fats and the proteins provide energy in a ratio of 3:1-1:1. Therefore, the serum albumin is an important source of nutrients for cell or body growth.

Ovalbumin (OVA) is a monomer phosphoglycoprotein consisting of 385 amino acid residues with nutritionally balanced amino acid compositions, and thus is an excellent dietary supplement. Therefore, the OVA is an important source of nutrients. In addition, each OVA molecule has an internal disulfide bond and four free thiol groups, can directly react with radicals, and thus has strong antioxidant activity. Compared with the serum albumin, the OVA is simpler in purification method, easier to obtain, and lower in cost, such that finding a simple alternative to animal serum albumin (BSA) to promote cell proliferation or maintain cell viability has important application values. Endocytosis is the basis for maintaining the life activities of an organism. Endocytosis is a key process of regulating nutrient internalization. Regulating the endocytosis efficiency of proteins facilitates the increasing of utilization of proteins by the organism or the cell, such that the normal growth of the cell is maintained. The bioavailability of nutrients is improved by improving the endocytosis efficiency of albumin. After intraluminal administration, Noah et. al. and Gustafsson et. al. observe OVA in the intestines, indicating that the OVA may undergo endocytosis in the intestines, which provide a good condition for the OVA to achieve a biological function and nutritional value. These research results indicate that the cell may internalize the OVA through endocytosis to achieve the nutritional value of the OVA. Improving the endocytosis efficiency of the OVA may facilitate the improvement of the biological function and the nutritional value of the OVA, such that certain theoretical support is provided for applications of the OVA in a cell culture medium and improvement of the nutritional value of the OVA. There is no suitable method for improving the endocytosis efficiency of a cell on OVA in the related art, such that there is an urgent need to develop a new method to promote cell proliferation and maintain cell viability.

SUMMARY

In view of the above problems, the present disclosure is intended to provide cell growth promoter and application thereof.

In order to achieve the above purpose, the present invention may adopt the following technical scheme:

A first aspect of the present disclosure provides a cell culture medium. The cell culture medium contains a $Fe^{2+}$-ovalbumin compound. The concentration of the $Fe^{2+}$-ovalbumin compound in the cell culture medium is 1 µg/mL-1000 µg/mL, includes but is not limited to, 100 µg/mL, 200 µg/mL, 250 µg/mL, 500 µg/mL, and 1000 µg/mL; and the cell culture medium does not contain amino acid and animal serum albumin.

Further, the cell culture medium also contains the cell culture medium excipients.

Preferably, the cell culture medium excipients include: $NaCl$, $KCl$, $NaHCO_3$, $KH_2PO_4$, $Na_2HPO_4$, glucose and/or water.

More preferred, the cell culture medium excipients include: 137.93 mM $NaCl$, 5.33 mM $KCl$, 4.17 mM $NaHCO_3$, 0.441 mM $KH_2PO_4$, 0.338 mM $Na_2HPO_4$, 5.56 mM glucose and/or water, and the pH values are 7.1-7.5.

Preferably, an animal serum albumin includes human serum albumin, a serum albumin, or bovine serum albumin.

A second aspect of the present disclosure provides a cell culture method, including culturing cells in the cell culture medium described in the first aspect.

The third aspect of the present disclosure provides a method for improving cell viability, by adding the cell growth promoter.

Further, the cells are mammalian cells. Preferably, the cells are mouse cells, pig cells, bovine cells, buffalo cells, sheep cells, goat cells, deer cells, wild ox cells, camel cells, red deer cells, rabbit cells, and/or human cells; more preferably, the cells are human cells.

And/or, the cells are epithelial cells, endothelial cells, macrophages, renal tubular cells, parenchymal liver cells, liver cells, myocardial cells, breast cancer cells, gastric cancer cells, lung cancer cells, hepatoma cells, cervical cancer cells, lymphatic cancer cells, thyroid cancer cells, esophageal cancer cells, renal cancer cells, pancreatic cancer cells, glioma cells, melanoma cells, bladder cancer cells, or prostate cancer cells.

The present disclosure has the following beneficial effects:

1. By means of the present disclosure, it is found that $Fe^{2+}$ may promote the endocytosis efficiency of the OVA, such that cell viability is improved, cell proliferation is promoted, and utilization of the OVA is increased.
2. By means of the present disclosure, it is found that by adding OVA bound to $Fe^2$, when the $Fe^{2+}$ and the OVA form a compound, the compound can maintain cell viability in an amino acid-free culture medium; and meanwhile, in an amino acid culture medium, cell proliferation can be promoted.
3. By means of the present disclosure, it is found that in the cell culture medium, the effect of the animal serum albumin can be replaced when the $Fe^{2+}$ and the OVA form the compound.

DETAILED DESCRIPTION OF THE EMBODIMENTS

Figure 1:
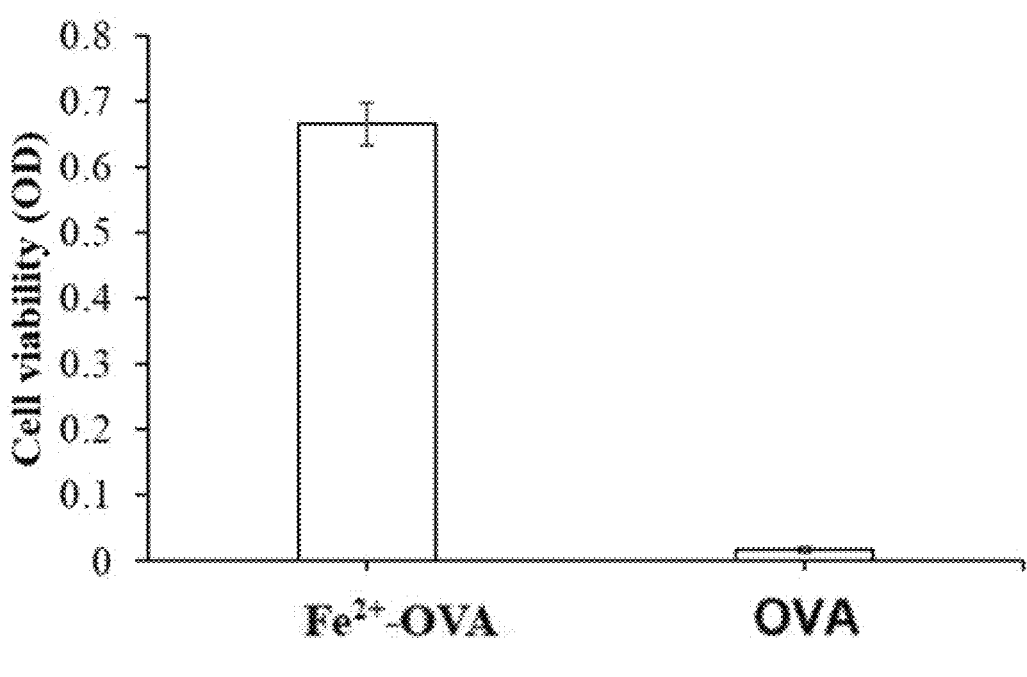
FIG. 1 shows comparison of the impact of $Fe^{2+}$-OVA and OVA on Caco-2 cell viability under conditions of amino acid starvation.

Unless otherwise defined, all scientific and technical terms used in the invention have the same meaning as generally understood by persons skilled in the technical field of the invention.

The embodiments of the invention will be described in detail below in combination with embodiments, but it will be understood by those skilled in the art that the following embodiments are used only used to illustrate the invention, and should not be considered to limit the scope of the invention. Where specific conditions are not specified in the embodiment, follow the conventional conditions or those recommended by the manufacturer. The reagents or instruments used that do not indicate the manufacturer are conventional products available through the market.

Experimental Method:

1.1 Westernblot Analysis 1.1.1 Protein Extraction

OVA containing different concentrations of $Fe^{2+}$ is used to treat Caco-2 cells and IEC-6 cells; after 4 h of treatment, supernatant is discarded; after washing is performed with PBS for 3 times, 100 µL of a cell lysis solution (containing 1 mM PMSF) is added to each well; a well plate is placed on ice and allowed to stand for 30 min, so as to extract proteins for determination of OVA endocytosis content. 3 parallel treatments are set for each group. The cells are scraped into a centrifuge tube by using a scraper in a clockwise direction, then centrifugation (4° C., 12000×g, 20 min) is performed, an upper layer protein extraction solution is sucked as a solution to be measured, so as to measure a total protein concentration and the level of a target protein in the extraction solution.

1.1.2 Determination of Total Protein Concentration in Extraction Solution 1.1.2.1 Preparation of Reagent:

1.1.2.1.1, 30% gel preparation solution (A solution): 29.2 g of acrylamide and 0.8 g of N,N-methylenebisacrylamide are weighed and placed in 80 mL of ultrapure water, and made up to 100 mL with the ultrapure water after being fully dissolved. The mixture is preserved at 4° C. for later use.

1.1.2.1.2, An SDS solution (10%, w/v): 10 g of SDS powder is weighed, fully dissolved, and made up to 100 mL with the ultrapure water.

1.1.2.1.3, 4× separation gel buffer solution (B solution): 75 mL of Tris-HCl (pH8.8) and 4 mL of 10% SDS are measured, and made up to 100 mL with the ultrapure water.

1.1.2.1.4, 4× stacking gel buffer solution (C solution): 50 mL of Tris-HCl (pH6.8) and 4 mL of 10% SDS are measured, and made up to 100 mL with the ultrapure water.

1.1.2.1.5, 1× electrophoretic buffer stock solution: 3 g of Tris, 14.4 g of glycine, and 1 g of SDS are weighted, made up to 1 L with the ultrapure water, and preserved at room temperature for later use.

1.1.2.1.6, 1× transmembrane buffer stock solution: 3 g of Tris, and 14.4 g of glycine, made up to 1 L with the ultrapure water, and preserved at room temperature for later use.

1.1.2.1.7, 1×TBS stock solution (pH7.5): 2.42 g of Tris-base and 8 g of NaCl are weighed and dissolved in 800 mL of the ultrapure water, the pH of the mixture is adjusted to 7.5 by adding hydrochloric acid after full dissolving, and then is made up to 1 L by adding the ultrapure water, 0.5 mL of tween 20 is added ultimately, and the mixture is fulled mixed and then preserved for later use.

1.1.2.1.8, Blocking solution: 5 g of defatted milk powder is weighed and dissolved in 100 mL of TBST, is well mixed through vibration and temporarily preserved at 4° C., and the blocking solution is prepared while being used.

1.1.2.2 A BCA protein detection kit (therom, 23227) is used to determine the concentration of total protein in an extracted protein sample.

1.1.2.2.1, Standard protein (2 mg/mL bovine serum albumin solution, buy from therom, 23227) is diluted with a lysis solution, and protein standard solutions of 0 mg/mL, 0.5 mg/mL, 0.75 mg/mL, 1 mg/mL, 1.5 mg/mL, and 2 mg/mL are successively obtained.

1.1.2.2.2, Working solution: 20 mL of a reagent 1 (1% disodium salt bicinchoninic acid, 2% anhydrous sodium carbonate, 0.16% sodium tartrate, 0.4% sodium hydroxide, and 0.95% sodium bicarbonate, a pH value being adjusted to 11.25 through mixing) and 400 µL of a reagent 2 (4% copper sulfate) are well mixed.

1.1.2.2.3, Sampling detection: 10 µL of the protein standard solution or a sample to be detected is added to each well, then 200 µL of the working solution is added, incubation is performed at 37° C. for 30 min. An OD value at 570 nm is determined after the end of incubation.

1.1.2.2.4, A standard curve of a protein concentration-OD value is plotted, and the total protein concentration in the extracted protein sample is calculated.

1.1.2.3 Sodium Dodecyl Sulfate-Polyacrylamide Gel Electrophoresis (SDS-PAGE)

The protein extraction solutions of all samples are adjusted to a uniform concentration, then 80 µL of the diluted protein extraction solutions (1, which are obtained by diluting the solution to be detected in the protein extraction step with the ultrapure water) are respectively taken, and 20 µL of a 5× sample-loading buffer solution is added and placed in a 95° C. metal bath for 10 min. The mixture is cooled and then preserved at −80° C. for later use.

According to the molecular weight of a target protein, in this embodiment, 10% separation gel and 4% stacking gel are used for protein sample separation. The separation gel and the stacking gel are prepared according to reagent volumes in Tables 1 and 2. Then the separation gel and the stacking gel are filled in a gel-making glass plate, and are allowed to stand at room temperature for 30 min for full solidification. 3 µL of protein markers are respectively added on two sides of a sample well. Electrophoresis conditions include: samples are first concentrated to a thin line of the same height at a constant pressure of 80 V, and then separated at a separation gel portion at a constant pressure of 120 V.

TABLE 1

| | | | | | |
|---|---|---|---|---|---|
| Method for preparing SDS-PAGE separation gel | | | | | |
| Separation gel concentration | A solution (mL) | B solution (mL) | Distilled water (mL) | TEMED (µL) | 10% AP (µL) |
| 10% | 3.335 | 2.5 | 4.15 | 10 | 100 |

TABLE 2

| | | | | | |
|---|---|---|---|---|---|
| Method for preparing SDS-PAGE stacking gel | | | | | |
| Separation gel concentration | A solution (mL) | C solution (mL) | Distilled water (mL) | TEMED (µL) | 10% AP (µL) |
| 4% | 0.53 | 1 | 2.47 | 0 | 30 |

Transmembrane and Antibody Incubation

A polyvinylidene difluoride (PVDF) membrane with a bore diameter being 0.45 µm is immersed in methanol for activation for 30 s, and is then placed in a transmembrane buffer solution. A black side of a transmembrane clip faces downward, and a transfer sponge-a transfer filter paper-a separation gel-a PVDF membrane-a transfer filter paper-a transfer sponge are successively placed from bottom to top. Transmembrane conditions are at a constant current of 200 mA for 2 h.

After transmembrane is completed, a side of the PVDF membrane that traps the protein faces upward, and is sealed overnight at 4° C. After sealing ends, the membrane is immersed in a primary antibody solution diluted to a proper concentration, and incubation is performed at 4° C. for 14 h, to as to cause a primary antibody to bind to the target protein. glyceraldehyde-3-phosphatedehydrogenase (GAPDH) or β-actin is used as an internal reference, and is diluted in a proportion of 1:1000. The primary antibody is recycled after the incubation ends, a TBST membrane-washing solution is used, the membrane-washing solution is changed every 10 min, and the cleaning step is repeated for 3 times to remove non-specifically bound antibodies. A secondary antibody (a dilution ratio being 1:4000) diluent is added, and incubation is performed at room temperature for 1 h. Then the TBST is used to repeat the same washing step, so as to remove the residual secondary antibody.

Development and Calculation of Relative Content of Target Protein:

a developer solution is prepared by mixing luminescent liquid in equal volumes of the A solution and the B solution; the developer solution (Beijing Huaxing Bochuang Gene Technology Co., LTD, HX1868) is uniformly coated on the membrane; and then a gel imager is used for development. ImageJ software is used to calculate the relative content of the target protein, and the relative content of the target protein is calculated according to a ratio of a gray value obtained by a target protein bank of each lane to a gray value of a corresponding internal reference protein band.

1.2 Immunofluorescence Staining

Specific steps are shown as follows.

1.2.1, HSA containing different contents of $Fe^{2+}$ is used to treat cells for 4 h, and then immersion cleaning is performed with PBS for 3 times, and is performed for 3 min each time.

1.2.2, 4% paraformaldehyde is used to fix the cells for 15 min, and then immersion cleaning is performed with PBS for 3 times, and is performed for 3 min each time.

1.2.3, 0.5% TritonX-100 is used to permeate the cells for 5 min, and then immersion cleaning is performed with PBS for 3 times, and is performed for 5 min each time.

1.2.4, An immunofluorescence blocking solution is used to block the cells for 30 min, and then the blocking solution is removed.

1.2.5, The primary antibody (a dilution ratio being 1:50) diluted to the proper concentration is added, and is incubated overnight at 4° C. The primary antibody diluent is removed, and then immersion cleaning is performed with PBST for 3 times, and is performed for 5 min each time.

1.2.6, well-diluted fluorescent secondary antibody (a dilution ratio being 1:500) is added and incubated at room temperature for 1 h, and the secondary antibody diluent is removed, and then immersion cleaning is performed with PBST for 3 times, and is performed for 5 min each time.

1.2.7, DAPI is added to stain cell nucleuses, incubation is performed for 5 min in dark, and the DAPI is removed, and then immersion cleaning is performed with PBST for 4 times, and is performed for 5 min each time.

1.2.8, Liquid on a climbing sheet is dried with an absorbent paper, a mounting medium containing fluorescent mounting media is dropped on a glass slide, then the climbing sheet is inverted onto the glass slide, and images are collected through a CLSM.

1.3 Transmission Electron Microscope

A cell culture medium is removed, and then washed and cleaned with PBS. A 2.5% glutaraldehyde solution is added, fixed overnight at 4° C., and then transferred to 1% osmic acid; and oscillation is performed for 3 h at 4° C. to immobilize the cells again. Then ethanol with different concentrations is used to perform dehydration on samples, after the ethanol is replaced with propylene oxide, the samples are then placed in epoxy resin, and immersed and embedded at 4° C.; and the samples are finally placed at 70° C. for 18 h to cause the resin to be polymerized to form a sample embedding block. The embedding block is cut into 60 nm slices, and an endocytosis process of HSA is observed by using a transmission electron microscope after staining.

Embodiment 1: Impact of $Fe^{2+}$ on Cell Viability and Endocytosis Efficiency (1) Caco-2 Cell Culture Preparation of a culture medium containing a solution ($Fe^{2+}$-OVA) of OVA bound to $Fe^{2+}$:$Fe^{2+}$ with a certain concentration was added to the OVA. The mixture was added to a centrifuge tube, then incubated at 37° C. for 15 min, and grouped into two groups, which were diluted by using a Hanks cell culture medium; a final concentration of the $Fe^{2+}$ is diluted to 22 µM, and a final concentration of the OVA is diluted to 22 µM; and in another group, only the OVA with the same concentration was added to the centrifuge tube (i.e., the $Fe^{2+}$ was not added), then incubated at 37° C. for 15 min, and diluted by using the Hanks cell culture medium, the final concentration of the OVA is diluted to 22 M, and cell states were observed at different times.

(2) Determination of Caco-2 Cell Endocytosis Efficiency of OVA

Preparation of a culture medium containing a solution ($Fe^{2+}$-OVA) of the OVA bound to the $Fe^{2+}$ with different concentrations: the OVA with a certain concentration and the $Fe^{2+}$ with different concentrations were respectively added to the centrifuge tube, then incubation was performed at 37° C. for 15 min, and finally, a compound was diluted by using the Hanks cell culture medium, so as to cause the final concentration of the $Fe^{2+}$ to respectively be 0 M, 22 M, 44 μM, 88 μM, and a final concentration of the OVA is diluted to 22 μM. The well-prepared culture mediums were respectively added to each well of a 12-well plate, after 4 h of treatment at 37° C., supernatant was discarded, washing was performed with ice PBS for 3 times, the well plate was placed on ice, proteins were extracted for Westernblot analysis (an analysis method referred to the foregoing "experimental method").

(3) Cell Activity Determination

An amino acid-free culture medium (Hanks culture medium) containing different concentrations of BSA, HSA, OVA, Fe2+-OVA or a culture medium (DMEM culture medium) rich in amino acids was used to culture Caco-2 cells for 24 h, then in-well culture media were discarded, 100 μL of a mixed solution of the DMEM culture medium and CCK-8 was added to each well again, incubation was performed at 37° C. for 1 h, and then OD values at 450 nm and 650 nm were determined to represent cell activity.

Experimental Result

As shown in FIG. 1, in the amino acid-free culture medium (Hanks culture medium), the culture medium only added with the OVA was unable to maintain the growth of the Caco-2 cells, the culture medium added with the OVA bound to the $Fe^{2+}$ was able to maintain the activity of the Caco-2 cells, and the OD value of the $Fe^{2+}$-OVA group was far greater than that of the OVA group, indicating that the binding to the $Fe^{2+}$ promotes the utilization of the OVA by the cells, such that the nutritional value of the OVA was increased, and cell activity was maintained.

Figure 2:
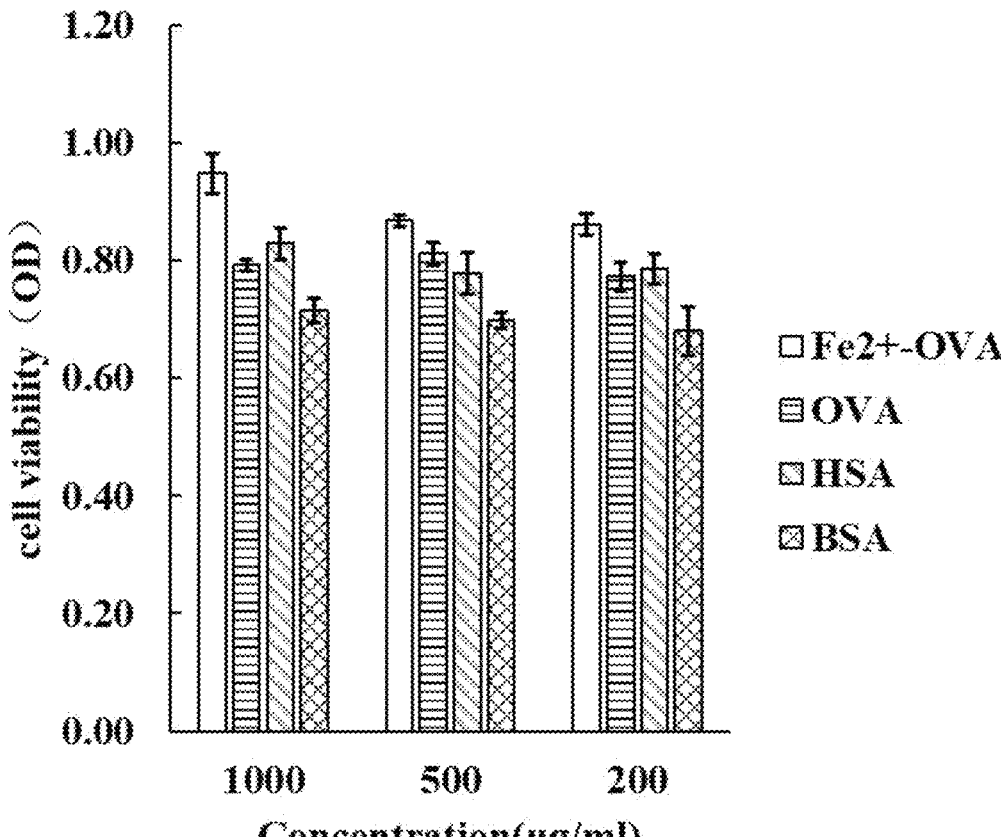
FIG. 2 shows the impact of HSA, BSA, OVA, $Fe^{2+}$-OVA in a culture medium on Caco-2 cell viability under conditions rich in amino acids.

As shown in FIG. 2, using BSA and HSA groups as positive controls, and using the OVA group and the $Fe^{2+}$-OVA group as experimental groups, in a culture medium environment rich in amino acids (DMEM), the OD value of the $Fe^{2+}$-OVA group was higher than that of the OVA, HSA, and BSA groups, i.e., the cell activity of the $Fe^{2+}$-OVA group was higher than that of the OVA, HSA, and BSA groups, indicating that pure OVA did not promote cell proliferation, and the OVA bound to the $Fe^{2+}$ ($Fe^{2+}$-OVA) in the culture medium rich in amino acids was still able to promote cell proliferation. Results showed that, $Fe^{2+}$-OVA was still able to maintain cell activity in an environment that is deficient in the amino acids, and was able to significantly promote cell proliferation under normal physiological conditions. In order to investigate the reason that the $Fe^{2+}$ improved the cell activity of the OVA, in this embodiment, the impact of the $Fe^{2+}$ on the endocytosis efficiency of the OVA was further detected, and a Westernblot technology was used to determine the impact of the OVA added with different doses of the $Fe^{2+}$ on the Caco-2 cells and the IEC-6 cells.

Figures 3A, 3B, 4:
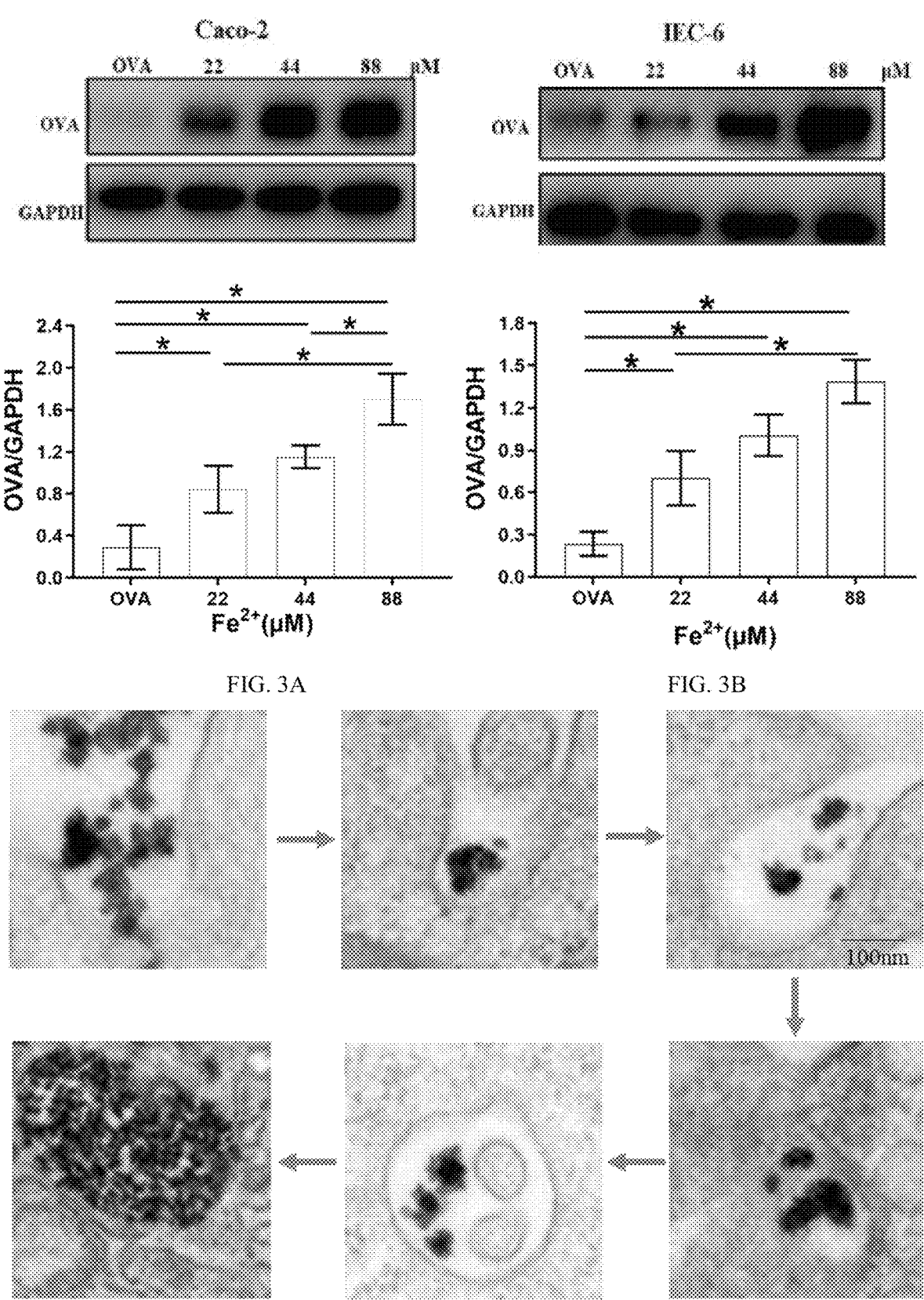
FIGS. 3A-3B show the impact of $Fe^{2+}$ on endocytosis efficiency of OVA.
FIG. 4 is a picture showing an endocytosis process of $Fe^{2+}$-OVA.

As shown in FIGS. 3A-3B, in order to investigate the impact of the $Fe^{2+}$ on the endocytosis efficiency of the OVA, the OVA with a certain concentration and the $Fe^{2+}$ with different concentrations were added to the centrifuge tube, then incubation was performed at 37° C. for 15 min, finally the $Fe^{2+}$-OVA was diluted by using the DMEM culture medium, the final concentrations of the $Fe^{2+}$ in each group of culture media were respectively diluted to 0 μM, 22 μM, 44 μM, and 88 μM, and the final concentration of the OVA in each group of culture media was diluted to 22 μM. The well-prepared $Fe^{2+}$-OVA culture mediums were respectively added to each well of a 12-well plate, after 4 h of treatment at 37° C., supernatant was discarded, washing was performed with ice PBS for 3 times, the well plate was placed on ice, proteins were extracted for Westernblot analysis.

As shown in FIGS. 3A-3B, with the increasing of the final concentration of the $Fe^{2+}$, the endocytosis efficiency of the OVA was significantly improved ($P<0.05$), indicating that the $Fe^{2+}$ improved the endocytosis efficiency of the OVA.

In order to further clear the endocytosis process of the OVA, in this embodiment, a TEM technology was used to photograph the process. As shown in FIG. 4, an endocytosis process of $Fe^{2+}$-OVA included: $Fe^{2+}$-OVA being bound to a cell membrane, then the cell membrane depressing inward to form endocytosis vesicles, then the vesicles falling off into cells, and the $Fe^{2+}$-OVA being located in intracellular bodies.

Figure 5:
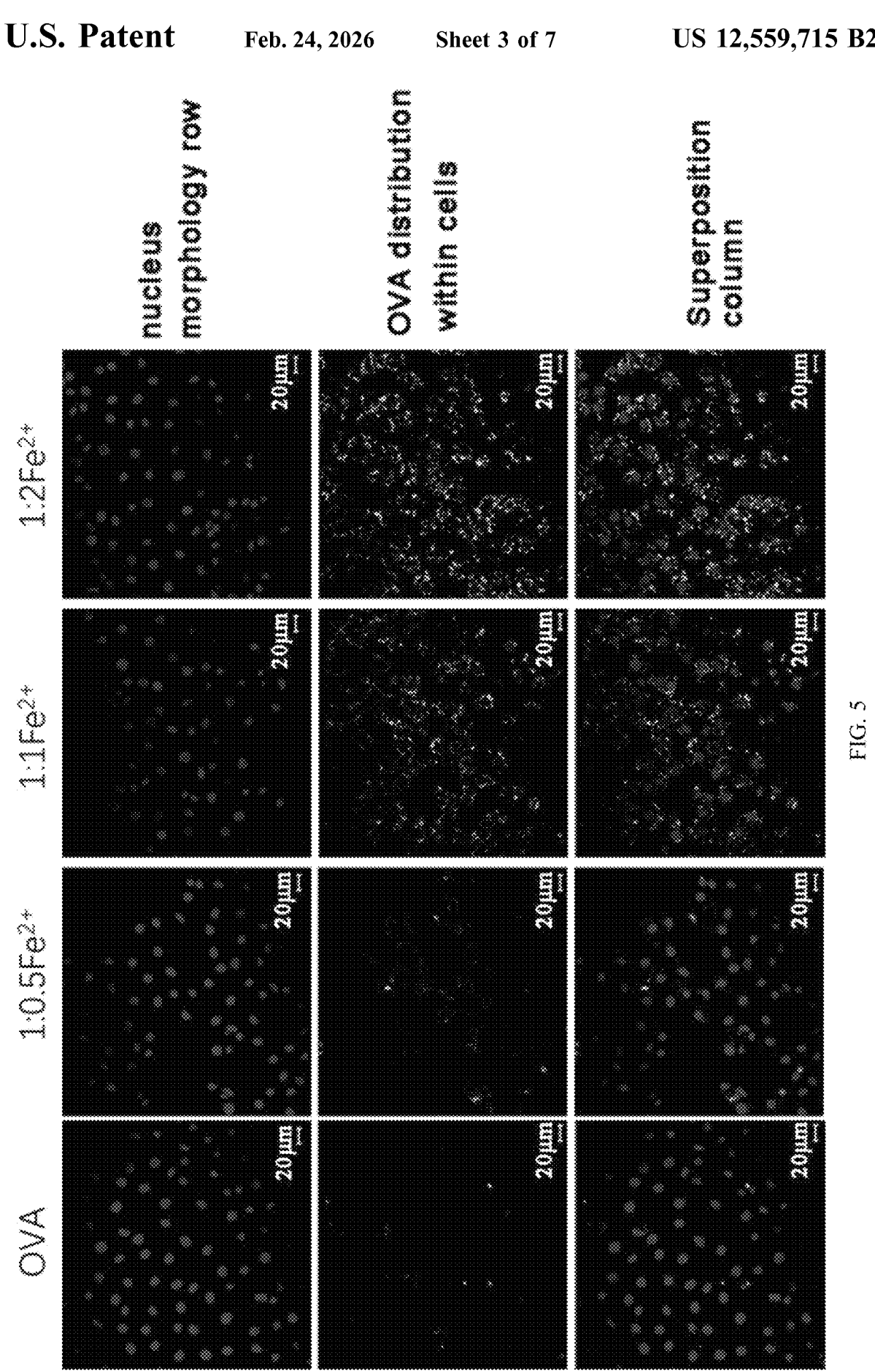
FIG. 5 is a fluorescence diagram of endocytosis of $Fe^{2+}$-OVA in an IEC-6 cell.

Embodiment 2: Impact of $Fe^{2+}$ on Endocytosis Efficiency of OVA in Different Types of Cells The foregoing embodiment indicated that the $Fe^{2+}$ promoted the endocytosis efficiency of the OVA in the Caco-2 cells. In order to study whether the promotion of OVA endocytosis by the $Fe^{2+}$ still had a promotion effect in different types of cells, an immunofluorescence method was used to determine the impact of an OVA and $Fe^{2+}$ compound on the endocytosis efficiency of rat intestinal epithelial cells (IEC-6). OVA, $1:0.5Fe^{2+}$, $1:1Fe^{2+}$, and $1:2Fe^{2+}$ in FIG. 5 respectively represented that the OVA was added separately, a molar ratio of OVA:$Fe^{2+}$ was 1:0.5, a molar ratio of OVA:$Fe^{2+}$ was 1:1, and a molar ratio of OVA:$Fe^{2+}$ was 1:2; and a DAPI dye was used to perform fluorescence labeling on cell nucleuses, and immunofluorescence staining was performed on the OVA in the cells. A light-colored circle in a nucleus morphology row represented the cell nucleuses, and the bright color in the OVA in a cell distribution row represented the amount of the OVA in the cells. From FIG. 5, it might be seen that, a fluorescent signal (i.e., the bright portion of the OVA in the cell distribution row) of the OVA gradually strengthened with the increasing of the dose of the $Fe^{2+}$, indicating that the $Fe^{2+}$ promoted the endocytosis efficiency of the OVA in the IEC-6 cells.

Figure 6:
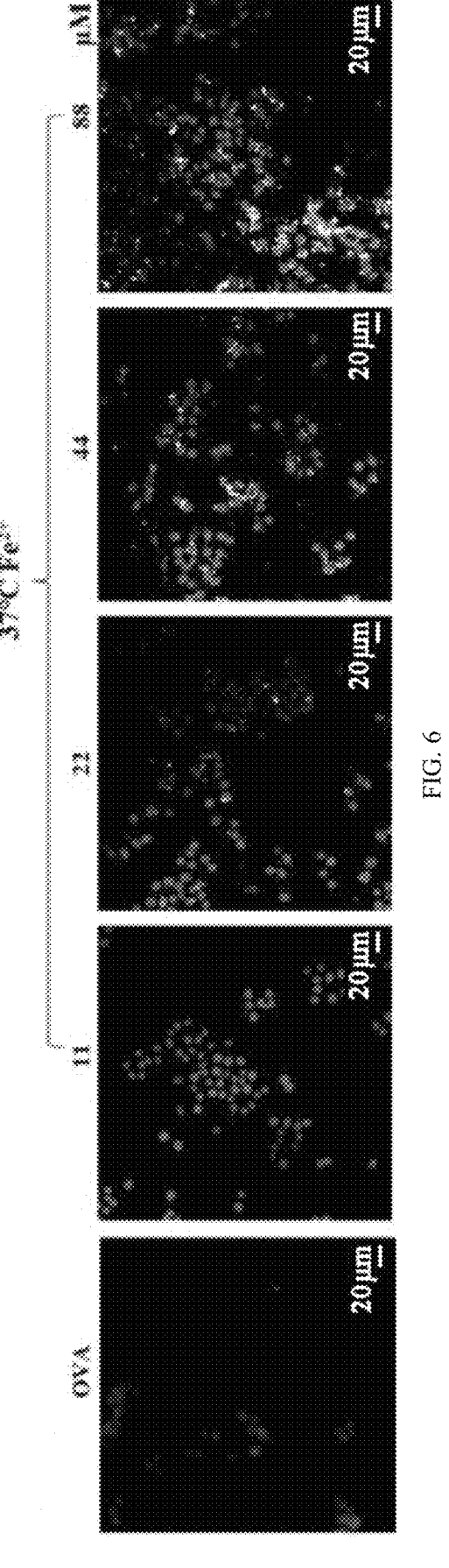
FIG. 6 is a fluorescence diagram of endocytosis of $Fe^{2+}$-OVA in a mouse mononuclear macrophage (RAW264.7).

In the present disclosure, the impact of the OVA and $Fe^{2+}$ compound on the endocytosis efficiency of a mouse mononuclear macrophage (RAW264.7) was further investigated, the DAPI dye was used to perform fluorescence labeling on cell nucleuses, and immunofluorescence staining was performed on the OVA in the cells. A round, medium-bright portion represented the cell nucleuses, and the brightest portion represented the content of the OVA in the cells (e.g., the brightest white dotted portion represented the OVA in the figure on the right 1 and right 2). A horizontal axis in FIG. 6 indicated, at 37° C., a group of OVA with the concentration being 22 μM, a group of OVA (with the concentration of the OVA being 22 μM) containing 11 μM $Fe^{2+}$, a group of OVA (with the concentration of the OVA being 22 μM) containing 22 μM $Fe^{2+}$, a group of OVA (with the concentration being 22 μM) containing 44 μM $Fe^{2+}$, a group of OVA (with the concentration being 22 μM) containing 88 μM $Fe^{2+}$. As shown in the group of OVA containing 44 μM $Fe^{2+}$ and the group of OVA containing 88 μM $Fe^{2+}$, it represented that the fluorescent signal (the brightest dotted portion) of the OVA gradually strengthened with the increasing of the dose of the $Fe^{2+}$, indicating that high-concentration $Fe^{2+}$ promoted the endocytosis efficiency of the OVA in RAW264.7 cells. These results proved once again that the $Fe^{2+}$ promoted endocytosis of the OVA, and had a promotion effect in different types of cells.

Embodiment 3: Combined Morphology of $Fe^{2+}$ and OVA

Experimental Procedure:

In order to verify whether the $Fe^{2+}$ and the OVA promoted endocytosis in a combined state, the impact of a $Fe^{2+}$ addition sequence on the endocytosis efficiency of the OVA was compared. A method for preparing a culture medium in the group "culture medium+$Fe^{2+}$+OVA" included: adding different concentrations of the $Fe^{2+}$ in the culture medium rich in amino acids, and then adding the OVA, where the final concentrations of the $Fe^{2+}$ in the system were respectively 5.5 µM, 11 µM, 22 µM and 44 µM, and the final concentration of the OVA was 22 µM.

A method for preparing a culture medium in the group "culture medium+$Fe^{2+}$-OVA" included: first preparing a solution of OVA bound to $Fe^{2+}$ ($Fe^{2+}$-OVA); and adding the OVA with different concentrations of $Fe^{2+}$ to a centrifuge tube, and then performing incubation at 37° C. for 15 min; finally, respectively using the culture media rich in amino acids to dilute a compound, until the final concentrations of the $Fe^{2+}$ were respectively 5.5 µM, 11 µM, 22 µM and 44 µM, and the final concentration of the OVA was 22 µM. And using westernblot to determine endocytosis efficiency.

Figure 9:
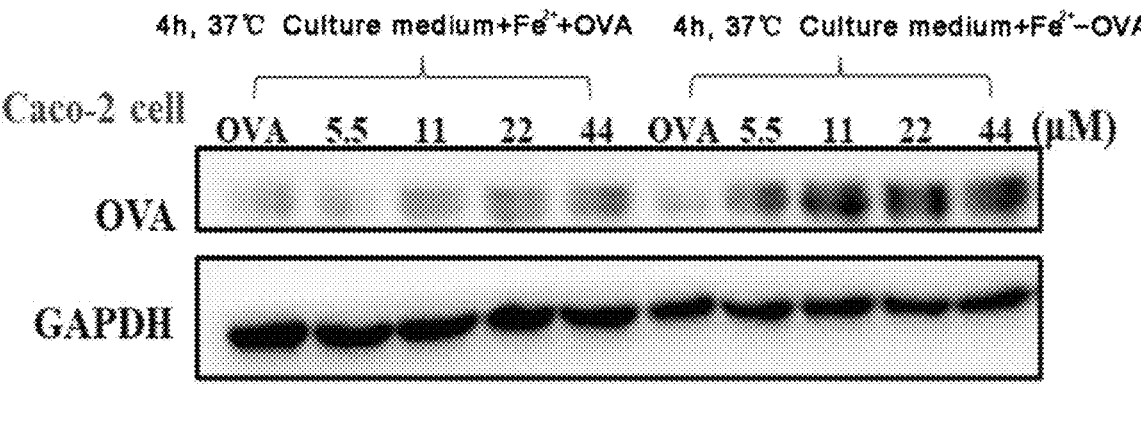
FIG. 9 shows the impact of a $Fe^{2+}$ addition sequence in Embodiment 3 on endocytosis efficiency of OVA.

Experimental Result:

If the $Fe^{2+}$ was first added to the culture medium rich in amino acids, the $Fe^{2+}$ first bound to amino acids in the culture medium, such that the binding efficiency of the $Fe^{2+}$ and the OVA was reduced. The solution of the OVA bound to the $Fe^{2+}$ was first prepared, it might be ensured that the $Fe^{2+}$ first bound to the OVA, so as to improve the binding efficiency. Therefore, in the present disclosure, the impact of adding different concentrations of $Fe^{2+}$ to the culture medium rich in amino acids followed by the OVA (with the concentration being 22 µM), and of preparing the solution of the OVA bound to the $Fe^{2+}$ followed by adding same to the culture medium on the endocytosis efficiency of the OVA were compared. From FIG. 9, it might be found that, a band in the group "culture medium+$Fe^{2+}$-OVA" is deeper than that in the group "culture medium+$Fe^{2+}$+OVA", such that it indicated that the content of the OVA endocytosed by cells treated by "culture medium+$Fe^{2+}$-OVA" was more than that by the cells treated by "culture medium+$Fe^{2+}$+OVA", proving that the endocytosis efficiency of the OVA was able to be promoted more efficiently after the $Fe^{2+}$ bound to the OVA.

Embodiment 4: Further Verification of Combined Morphology of Fe2+ and OVA

Figure 10:
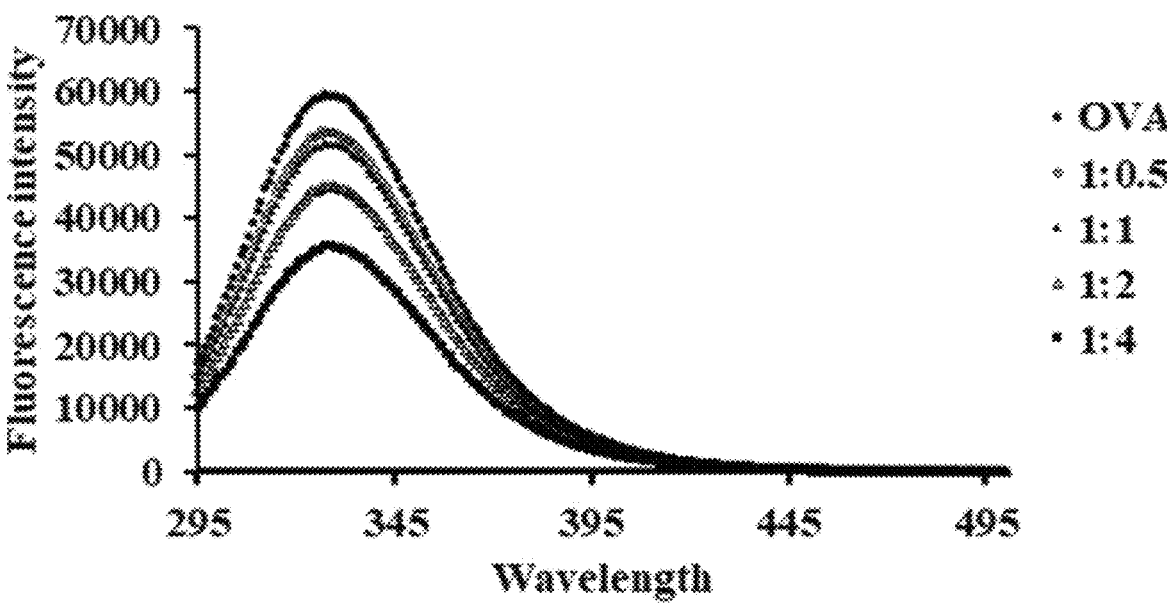
FIG. 10 is a diagram of a fluorescence quenching result of OVA added with different concentrations of $Fe^{2+}$ in Embodiment 4, and the legend represents a molar ratio of the OVA to the $Fe^{2+}$.

Experimental Procedure:

A certain amount of OVA was weighed and dissolved in a 10 mM $Na_2HPO_4$/$KH_2PO_4$ buffer solution, the final concentrations of the OVA was 22 µM, certain amount of a solution containing $Fe^{2+}$ was taken to the OVA until the final concentrations of the $Fe^{2+}$ were respectively 11 µM, 22 µM, 44 µM and 88 µM, reaction was performed at 37° C. for 15 min, and the mixture was prepared while being used. 1:0.5, 1:1, 1:2 and 1:4 in FIG. 10 respectively represented molar ratios of the OVA to the $Fe^{2+}$ in the system, and the OVA represented the absence of the $Fe^{2+}$.

Experimental Result:

In the present disclosure, a fluorescence spectroscopy was used to determine a fluorescence quenching spectrum of the OVA added with different concentrations of the $Fe^{2+}$. As shown in FIG. 10, a fluorescence quenching degree of the OVA gradually increased with the increasing of the concentration of the $Fe^{2+}$, which might be due to the formation of non-fluorescent complexes between the $Fe^{2+}$ and HSA, resulting in a fluorescence burst effect of the OVA, indicating that the $Fe^{2+}$ might interact with the OVA.

Comparative Example 1: Impact of Different Types of Divalent Cation on Endocytosis of OVA The Efficiency of $Mg^{2+}$ on Cell Endocytosis of OVA:

Cell culture: preparation of a culture medium containing a solution of the OVA bound to the $Mg^{2+}$ ($Mg^{2+}$-OVA) with different concentrations: the OVA with a certain concentration and the $Mg^{2+}$ with different concentrations were respectively added to the centrifuge tube, molar ratios of OVA protein to $Mg^{2+}$ ions were respectively 1:1, 1:2, 1:4, 1:8, 1:10 and 1:20, then incubation was performed at 37° C. for 15 min, and finally, a compound was diluted by using a DMEM culture medium, so as to cause the final concentration of the $Mg^{2+}$ to respectively be 0 µM, 22 µM, 44 µM, 88 µM, 176 µM, 220 µM, and 440 µM, and the final concentration of the OVA was 22 µM. The well-prepared culture mediums were respectively added to each well of a 12-well plate, after 4 h of treatment at 37° C., supernatant was discarded, washing was performed with ice PBS for 3 times, the well plate was placed on ice, proteins were extracted for Westernblot analysis.

Figure 7:
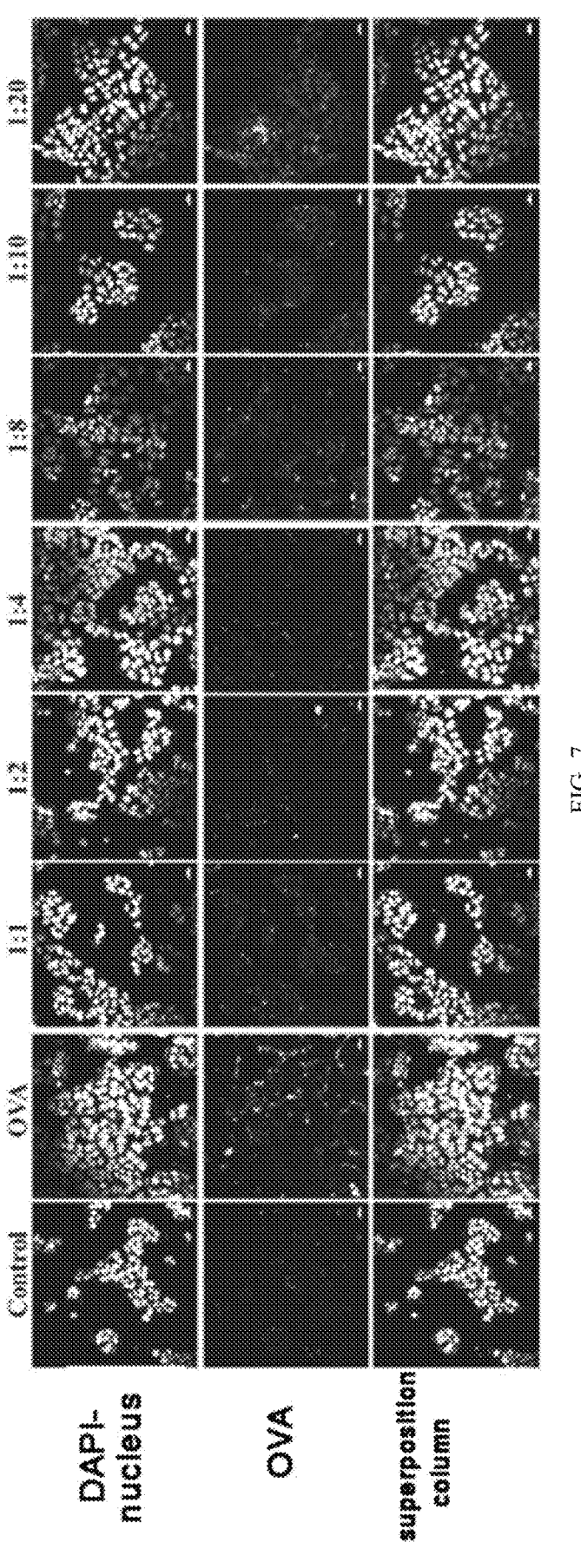
FIG. 7 is a fluorescence diagram of the impact of $Mg^{2+}$ on endocytosis efficiency of OVA.

Horizontal coordinates in FIG. 7 respectively indicated from left to right: a Control group (only added with the DMEM culture medium), an OVA group (with the concentration being 22 µM), and a group in which a molar ratio of the OVA to the $Mg^{2+}$ was 1:1 (i.e., a final concentration of the OVA being 22 µM+a final concentration of the $Mg^{2+}$ being 22 µM), a group in which a molar ratio of the OVA to the $Mg^{2+}$ was 1:2 (i.e., a final concentration of the OVA being 22 µM+a final concentration of the $Mg^{2+}$ being 44 µM), a group in which a molar ratio of the OVA to the $Mg^{2+}$ was 1:4 (i.e., a final concentration of the OVA being 22 µM+a final concentration of the $Mg^{2+}$ being 88 µM), a group in which a molar ratio of the OVA to the $Mg^{2+}$ was 1:8 (i.e., a final concentration of the OVA being 22 µM+a final concentration of the $Mg^{2+}$ being 176 µM), a group in which a molar ratio of the OVA to the $Mg^{2+}$ was 1:10 (i.e., a final concentration of the OVA being 22 µM+a final concentration of the $Mg^{2+}$ being 220 µM), a group in which a molar ratio of the OVA to the $Mg^{2+}$ was 1:20 (i.e., a final concentration of the OVA being 22 µM+a final concentration of the $Mg^{2+}$ being 440 µM). A DAPI dye was used to perform fluorescence labeling on cell nucleuses, and immunofluorescence staining was performed on the OVA in the cells. The round bright portion of a DAPI-nucleus row indicated the cell nucleuses, the bright portion of an OVA row indicated the distribution of the OVA in the cells, and a superposition column referred to a result of superimposing two fluorescent signals together. With the increasing of an addition ratio of the $Mg^{2+}$, it indicated that there was no significant change in the fluorescent signal of the OVA, indicating that the $Mg^{2+}$ had no significant effect on the efficiency of endocytosis of the OVA.

Figure 8:
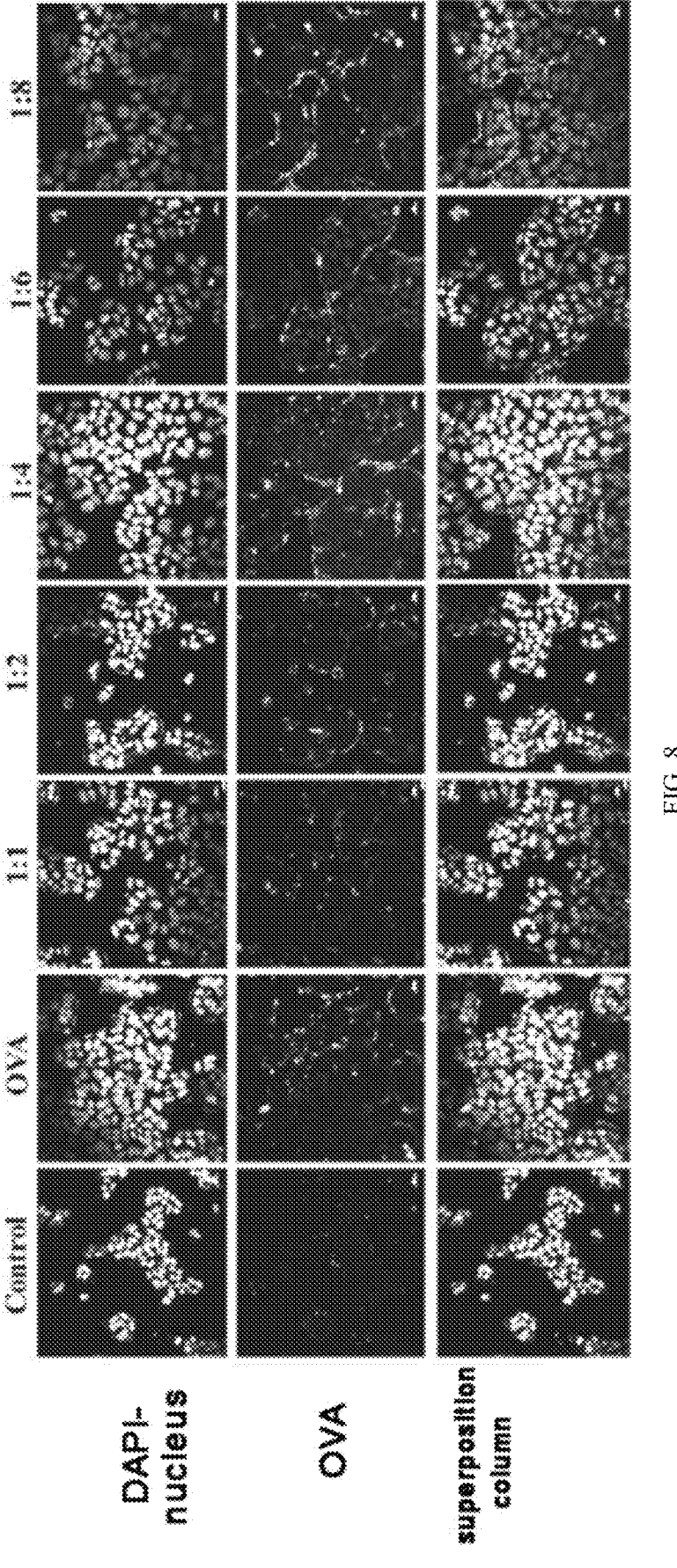
FIG. 8 is a fluorescence diagram of the impact of $Ca^{2+}$ on endocytosis efficiency of OVA.

The Efficiency of $Ca^{2+}$ on Cell Endocytosis of OVA:

An experimental method referred to Embodiment 1 to determine the impact of the addition of different doses of $Ca^{2+}$ on Caco-2 cell endocytosis efficiency of the OVA. Horizontal coordinates in FIG. 8 respectively indicated from left to right: a Control group (only added with the DMEM culture medium), an OVA group (with the concentration of the OVA being 22 μM), and a group in which molar ratios of the OVA to the $Ca^{2+}$ were respectively 1:1 (i.e., a final concentration of the OVA being 22 μM+a final concentration of the $Ca^{2+}$ being 22 μM), 1:2 (i.e., a final concentration of the OVA being 22 μM+a final concentration of the $Ca^{2+}$ being 44 μM), 1:4 (i.e., a final concentration of the OVA being 22 μM+a final concentration of the $Ca^{2+}$ being 88 μM), 1:8 (i.e., a final concentration of the OVA being 22 μM+a final concentration of the $Ca^{2+}$ being 176 μM), 1:10 (i.e., a final concentration of the OVA being 22 μM+a final concentration of the $Ca^{2+}$ being 220 μM), and 1:20 (i.e., a final concentration of the OVA being 22 μM+a final concentration of the $Ca^{2+}$ being 440 μM). A DAPI dye was used to perform fluorescence labeling on cell nucleuses, and immunofluorescence staining was performed on the OVA in the cells. The round bright portion of a DAPI-nucleus row indicated the cell nucleuses, the bright portion of an OVA row indicated the distribution of the OVA in the cells, and a superposition column referred to a result of superimposing two fluorescent signals together. With the increasing of the dose of the $Ca^{2+}$, it indicated that there was no significant change in the fluorescent signal of the OVA, and the $Ca^{2+}$ had no effect on the endocytosis efficiency of the OVA.

In summary, in the present disclosure, it was found that, compared with individual OVA or bovine serum albumin, the OVA bound to the $Fe^{2+}$ was able to be used by more cells, such that the growth of the cells might be still maintained in the amino acid-free culture medium, and cell proliferation might be still promoted in the culture medium rich in amino acids. In order to further investigate a mechanism of promoting cell proliferation, in the present disclosure, the impact of the $Fe^{2+}$ on the endocytosis efficiency of the OVA was further determined, and it was found that the $Fe^{2+}$ might promote the endocytosis efficiency of the OVA, which might be a main reason that the OVA bound to the $Fe^{2+}$ promoted cell proliferation, so as to provide more choices for the development of cell culture media.

Finally, it should be noted that the above embodiments are only used to explain the technical scheme of the invention, not to the detailed description of the embodiments, the ordinary technicians in the art should understand that it can still modify the technical solutions recorded in the embodiment or replace some or all of the technical features; and these modifications or replacement do not separate the essence of the corresponding technical solutions from the scope of the various embodiments of the invention.

What is claimed is:

1. A method for improving a cell viability, comprising the steps of preparing a $Fe^{2+}$-ovalbumin (OVA) compound by adding a solution of OVA to a solution of $Fe^{2+}$ and incubating at 37° C. for 15 minutes, wherein a molar ratio of the OVA to the $Fe^{2+}$ is 1:0.5-4;

diluting the $Fe^{2+}$-OVA compound in cell culture medium, wherein a final concentration of $Fe^{2+}$ added is 10-100 μM, and a final concentration of OVA added is 10-100 μM; and adding the cell culture medium containing the $Fe^{2+}$-OVA compound to a mammalian cell, wherein the method is for non-diagnostic or non-therapeutic purposes.

2. The method for improving the cell viability according to claim 1, wherein the method is performed in an environment being free of an amino acid or animal serum albumin.

3. The method for improving the cell viability according to claim 1, wherein in the method, an animal serum albumin is replaced with the $Fe^{2+}$-OVA compound.

* * * * *